United States Patent [19]

Freedman et al.

[11] Patent Number: 5,501,971
[45] Date of Patent: Mar. 26, 1996

[54] METHOD AND APPARATUS FOR ANCHORAGE AND SUSPENSION CELL CULTURE

[75] Inventors: David Freedman; Guozheng Wang, both of Highland Park, N.J.; Avinoam Kadouri, Petach-Tiqua, Israel

[73] Assignee: New Brunswick Scientific Co., Inc., New Brunswick, N.J.

[21] Appl. No.: 346,830

[22] Filed: Nov. 30, 1994

Related U.S. Application Data

[63] Continuation of Ser. No. 11,350, Jan. 29, 1993, abandoned.

[51] Int. Cl.$^6$ .................................. C12N 5/00; C12M 3/00
[52] U.S. Cl. .................................. 435/240.23; 435/293.2; 435/295.1; 435/295.2; 435/302.1
[58] Field of Search .................. 435/240.23, 240.24, 435/240.4, 284–286, 288, 299, 313–316, 813; 422/211, 218, 311; 210/615–617, 150, 151

[56] References Cited

U.S. PATENT DOCUMENTS

| | | | |
|---|---|---|---|
| 3,966,599 | 6/1976 | Burkhead | 210/150 |
| 3,980,561 | 9/1976 | Miyagi et al. | 210/151 |
| 4,087,327 | 5/1978 | Feder et al. | |
| 4,343,904 | 8/1982 | Birch et al. | 435/285 |
| 4,634,675 | 1/1987 | Freedman et al. | 435/286 |
| 4,649,114 | 3/1987 | Miltenburger et al. | 435/284 |
| 4,727,040 | 2/1988 | Freedman et al. | 435/315 |
| 4,833,083 | 5/1989 | Saxena | 435/284 |
| 4,888,294 | 12/1989 | Van Wezel et al. | 435/316 |
| 4,906,577 | 3/1990 | Armstrong et al. | 435/313 |
| 4,921,792 | 5/1990 | Trawinski et al. | 435/41 |
| 4,963,490 | 10/1990 | Churchouse et al. | 435/284 |
| 5,019,512 | 5/1991 | Varecka et al. | 435/284 |
| 5,079,161 | 1/1992 | Mitsuda et al. | 435/285 |
| 5,081,036 | 1/1992 | Familletti | 435/286 |
| 5,096,814 | 3/1992 | Aivasidis et al. | 435/41 |
| 5,100,783 | 3/1992 | Dean, Jr. et al. | 435/69.1 |
| 5,100,799 | 3/1992 | Mundt | 435/174 |
| 5,114,853 | 5/1992 | Hu et al. | 435/174 |
| 5,126,269 | 6/1992 | Fike et al. | 435/284 |

FOREIGN PATENT DOCUMENTS

| | | |
|---|---|---|
| 2059367 | 7/1992 | Canada. |
| 3818776 | 12/1989 | Germany. |
| 2178447 | 12/1989 | United Kingdom. |
| 9100339 | 1/1991 | WIPO. |

OTHER PUBLICATIONS

Animal Cells—The Breakthrough to a Dominant Technology, Brian Griffiths Division of Biologics, PHLS CAMR, Cytotechnology 3: 109–116, 1990.

*Primary Examiner*—William H. Beisner
*Attorney, Agent, or Firm*—Richard C. Woodbridge

[57] ABSTRACT

A method and apparatus cultivates anchorage and nonanchorage cell in a reactor. A reactor includes a basket type packed bed and an internal recirculation device. The basket includes a top and bottom portion for allowing medium to flow uniformly through the basket. Medium flows downwardly from the top of the basket through the basket for providing gentle flow and preventing removal of cells from the carrier. Preferably, the carrier is formed of a fiber matrix.

12 Claims, 7 Drawing Sheets

METHOD AND APPARATUS FOR ANCHORAGE AND SUSPENSION CELL CULTURE

This application is a continuation of application Ser. No. 08/011,350, filed Jan. 29, 1993, now abandoned.

BACKGROUND OF THE INVENTION

1. Field of the Invention

This invention relates to a method and apparatus for cultivating anchorage and nonanchorage dependent cells.

2. Description of the Related Art

The cultivating of cells is desired for a variety of purposes such as for the production of hormones, enzymes, antibodies, vaccines and the like. Certain cell lines are anchorage dependent as is well known in the art. This means that the cells must adhere and grow as monolayers and multilayers anchored to a glass or plastic substrate.

Culture of anchorage dependent cells has conventionally been performed by attaching the cells to stacked petri dishes or by growing the cells in roller bottles. These approaches have the drawbacks of being unable to achieve high volumetric cell density or of having inadequate circulation necessary to the growth of the cells. In addition, cells tend to detach from their anchorage surface under conditions such as high or low serum concentrations, monolayer saturation or viscous sheer caused by stirring or perfusion of the culture medium.

Alternative methods have been suggested for increasing the surface area for attachment to increase proliferation of cells. Microcarrier systems have been described in which minute beads are formed of a specific gravity such that the beads float in culture fluid under gentle agitation. Once suspended, cells attach, spread and grow on the external surface of the microcarriers.

In particular, U.S. Pat. No. 5,114,855 describes using a microcarrier formed of microspheres. The microspheres have a diameter of less than about 60 µm. Microcarrier systems have the disadvantage in that the necessity for suspension and mixing creates handling problems. Also, cells are subjected to mechanical stress which might result in cell rupture.

It is also known that certain types of cells can be grown in suspension. Suspension cell lines conventionally have been grown using a stirred-tank reactor. For certain applications, these suspension cells can be conveniently cross-linked to a solid matrix or encapsulated in gelatin, alginate, agarose, etc. to protect the cells from mechanical stress.

Conventional immurement methods have been used for facilitating the harvesting of cells in suspension culture. Examples of immurement techniques are: hollow fiber (Hopkinson, J. "Hollow Fiber Cell Culture Systems For Economical Cell-Product Manufacturing", Bio/Technology 3: 225–230 (1985)); and membrane reactors (Scheirer, W., "High Density Growth of Animal Cells Within Cell Retention Fermentors Equipped with Membranes", In: Spier, R. E. and Griffiths, J. B. (Eds.) Animal Cell Biotechnology, Vol. 3, pp. 263–281 (1988)). These techniques have the disadvantage that scale-up of these methodologies is difficult.

In addition, entrapment methods can be used for entrapping non-anchorage dependent cells within a matrix. A matrix used for entrapping cells is described in UK Patent No. GB 2178447. This patent describes a matrix of a nonwoven fabric having a pore diameter of from 10 µm to 100 µm for providing high internal volume with pores that are 1 to 20 times the volume of individual cells. A porous support sheet can be bonded to the matrix for providing dimensional stability and physical strength. The matrix sheets are used as liners for the bottom of petri dishes or are wound into a spiral and immersed in a container of medium. The matrix can also be used for growing anchorage dependent cells.

Packed bed reactors for the cultivation of anchorage dependent cells have been in use for many years. A packed bed bioreactor for growing either anchorage or nonanchorage dependent cells has also been described in U.S. Pat. No. 4,833,083. In this patent, a vessel contains a packed bed of a support or matrix material. Cells or cell components attach or are entrapped to the solid support material or matrix material of the packed bed. The solid support material is formed of diatomaceous earth, silica, alumina, ceramic beads, charcoal, polymeric beads or glass beads. Medium is pumped horizontally inwardly across the packed bed for radial flow of the medium through the packed bed.

Of possible general relevance are U.S. Pat. Nos. 5,081,036, 4,888,294, 5,100,799 and 5,019,512 related to impellers for generating flow of the medium within the cell culture. Other patents of possible general relevance to the invention are U.S. Pat. Nos. 4,087,327, 4,906,577, 5,079,161 and 5,126,269, 4,727,040 and 4,634,675 related to attachment surfaces and bioreactors.

A need exists for a device in which cells are protected against mechanical stress and the cells are provided with optimum levels of nutrients and oxygen. The highest possible cell densities or concentrations are needed to achieve economical and large quantity production of the cells of interest.

SUMMARY OF THE INVENTION

Briefly described, the present invention comprises an improved reactor for fermentation and tissue culturing for both anchorage and non-anchorage dependent cells. The reactor is designed as a packed bed with a means which provides internal recirculation. Preferably, a fiber matrix carrier is placed in a basket within a reactor vessel. A top and bottom portion of the basket has holes therethrough for allowing medium to flow uniformly through the basket.

A recirculation means provides flow of medium through the space occupied by the fiber matrix for assuring a uniform supply of nutrients and the removal of wastes while simultaneously assuming that a negligible amount of the total cell mass is suspended in the medium. The combination of the basket and the recirculation means also provides a bubble free flow of oxygenated medium through the fiber matrix.

In comparison to other culturing systems, the present invention offers several significant advantages. With a fiber matrix carrier, the cells are protected against mechanical stresses such as agitation and foaming. The free medium flow through the basket provides the cells with optimum regulated levels of oxygen, pH and nutrients. The product can be continuously removed from the culture. The harvested product is free of cells and produced in low-protein medium which makes subsequent purification steps easier. Also, the unique design of this invention offers an easier way to scale-up the reactor.

DETAILED DESCRIPTION OF THE INVENTION

During the course of this description like numbers will be used to identify like elements according to the different figures which illustrate the invention.

Figure 1:
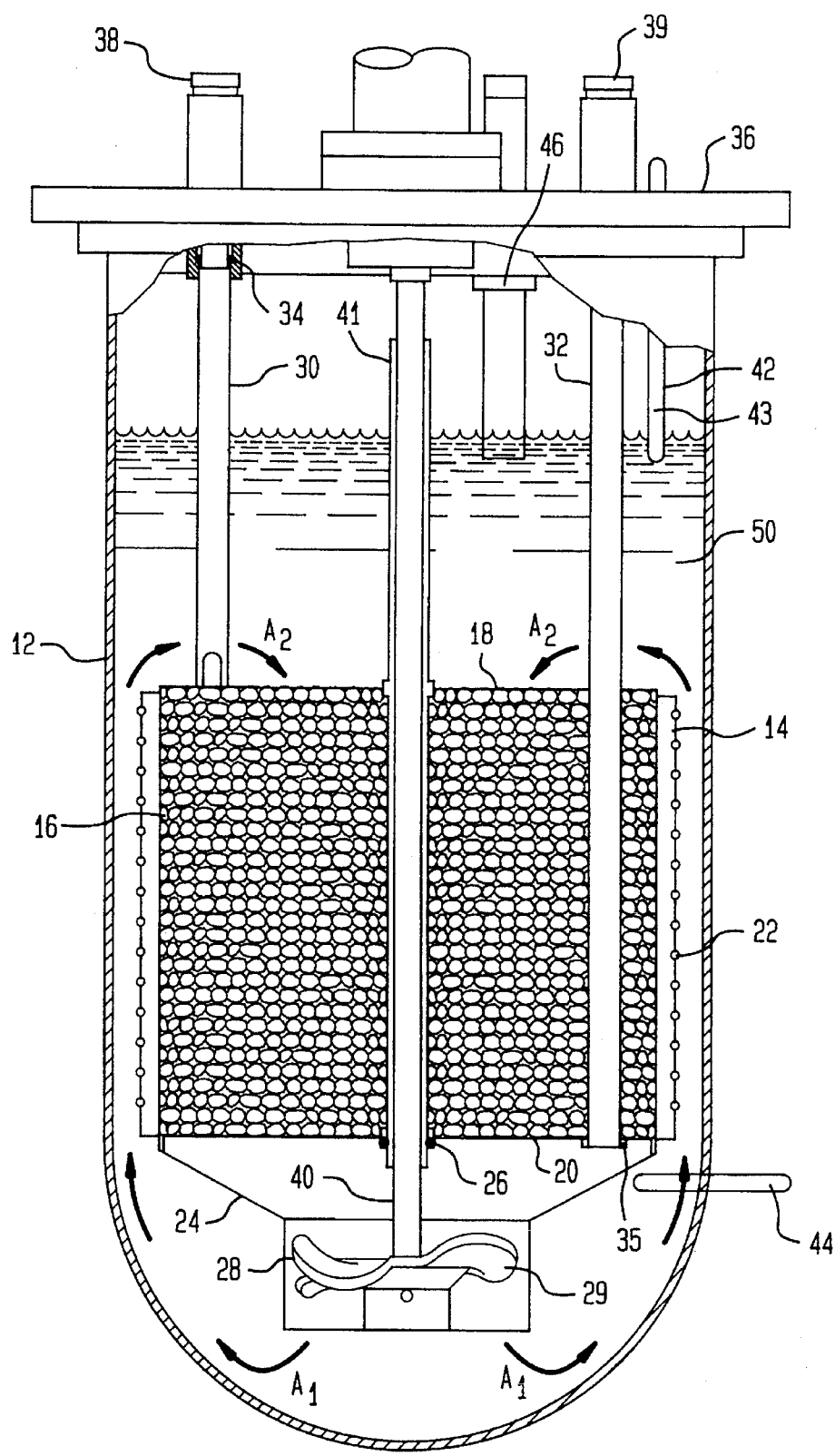
FIG. 1 is a front elevational view of a first embodiment of the reactor of the present invention.

FIG. 1 illustrates reactor 10 of a first embodiment of the present invention. Reactor 10 includes vessel 12 and basket 14 disposed within the vessel. Carrier material 16 is positioned within basket 14. Screens 18 and 20 form the top and bottom portions of basket 14 and allow flow of medium through basket 14. Screens 18 and 20 are preferably formed of stainless steel. Preferably, permeable silicone tubing forms sides 22 of basket 14 for enabling spent medium 50 to be dispensed from the basket.

Cover 24 is attached to the lower surface of screen 20 for directing medium 50 which has passed through basket 14 to impeller 28. Impeller 28 is rotated by shaft 40 for circulating medium 50 which has passed through basket 14. Impeller 28 includes downwardly facing blade 29 pushing medium away from basket 14 in direction $A_1$. Medium 50 flows upwards between vessel 12 and sides 22 of basket 14. Thereafter, medium 50 flows in a downwardly direction $A_2$ through screen 20 and through basket 14. O-ring 26 seals basket 14 to immersed housing 41.

Additionally, impeller 28 can rotate at varying speeds depending on the needs of the system. In particular, the preferred rotation speed is between about 20 to about 225 rpm. The preferred flow rate is between about 0.2 to 2.5 cm/s. A working volume of 1.0 to 1000 liters can be used with the reactor. The preferred working volume is about 2.5 to about 5.0 liters.

Head plate 36 can be removed for introduction of the carrier and cells into vessel 12. Plugs 38, 39 extend from the upper surface of head plate 36 and receive medium during cell cultivation. Top guiding tube 30 is attached with O-ring 34 to plug 38 for directing medium to the top of basket 14. Bottom guiding tube is attached with O-ring 35 to plug 39 for directing medium to the bottom of basket 14.

Vessel 12 is provided with probe 42 attached to head plate 36 for measuring dissolved oxygen. Tip 43 of probe 42 extends below the surface of medium 50 above basket 14. A second dissolved oxygen probe 44 is positioned below basket 14. A pH probe 46 is attached to head plate 36. It will be appreciated that other sensors and control devices can be used with the present invention.

Figure 2:
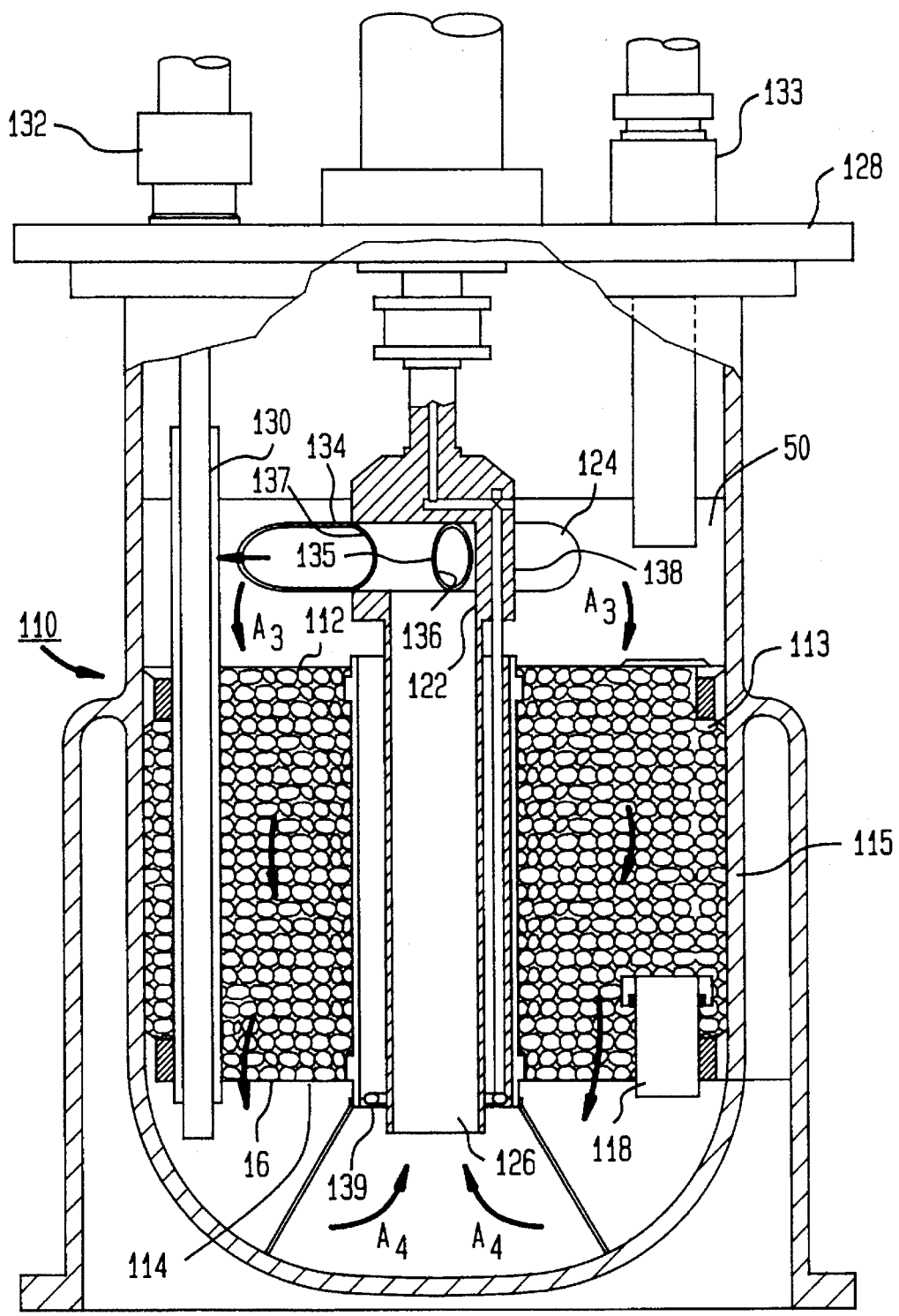
FIG. 2 is a front elevational view of a second embodiment of the reactor of the present invention.

FIG. 2 illustrates reactor 100 of a second embodiment of the present invention. Vessel 110 houses packed bed 113 of carrier material 16. Top screen 112 and bottom screen 114 surround packed bed 113. Packed bed 113 extends on either side of hollow shaft 126 to inside wall 115 of vessel 110. Port 132 aspirates PBS and medium through aspirating tube 130. Spent medium is removed from vessel 110 by tube 133. Aspirating tube 130 extends through packed bed 113 to the bottom of vessel 110.

Agitator 124 is attached to end 122 of hollow shaft 126. Agitator 124 includes tubulations 134 which project laterally from hollow shaft 126. Tubulations 134 are hollow and include a first end 135 defining an exit opening 136 and a second end 137 connected to an opening 138 in the hollow shaft 126. Fluid flows through hollow shaft 126 and exits through tubulations 134 out exit openings 136. Agitator 124 operates in a manner consistent with the agitator described in U.S. Pat. No. 4,634,675 (the '675 patent) for creating a suction effect, the '675 patent is incorporated herein by reference. Agitator 124 directs fluid flow from exit openings 136 in downward direction $A_3$ through packed bed 113. Agitator 124 also sucks medium through hollow shaft 126 for directing flow of medium in direction $A_4$ upwardly through hollow shaft 126. The above-described reactors provide for flow and aeration of cell structures attached to a carrier positioned in the basket while minimizing detachment of the cells from the carriers. Air is introduced from sparger 139 at the bottom hollow shaft 126 for providing an oxygenated medium and disengaging the bubbles at the upper fluid surface. Agitator 124 provides a recirculation means for providing bubble-free medium to the packed bed basket. The basket protects cells from turbulence created at higher stirring rates thereby providing greater oxygen exchange to increase cell growth.

In this embodiment, carrier 16 is a non-woven material. However, other materials such as polyester, nylon and inorganic materials can also be used.

Figure 4A:
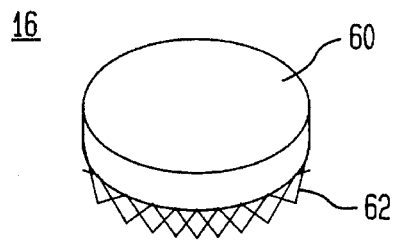
FIG. 4A is a front elevational view of a carrier of the present invention.
Figure 4B:
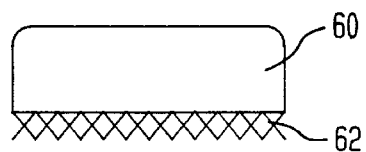
FIG. 4B is a side elevational view of the carrier shown in FIG. 4.

In the alternative, carrier material 16 can be formed of a plurality of disks, as illustrated in FIG. 4A. Carrier 16 has a contoured upper surface 60, as shown in FIG. 4B. Upper surface 60 is raised a height of about 0.005 inch to about 0.015 inches above lower surface 62. Carrier 16 has a disk shape with a diameter of about 3/16 to about 3/8 of an inch.

Lower surface 62 of carrier 16 is formed of a non-woven screen material of a network of fibers. Examples of a screen material useful for practicing the invention include polyethylene, polypropylene and Teflon®. Teflon® is a registered trademark of Dupont, Del. It will be appreciated that other non-woven materials for the carrier and screen can be used within the teachings of the present invention. Lower surface 62 can be laminated or bolted to upper surface 60.

Figure 3:
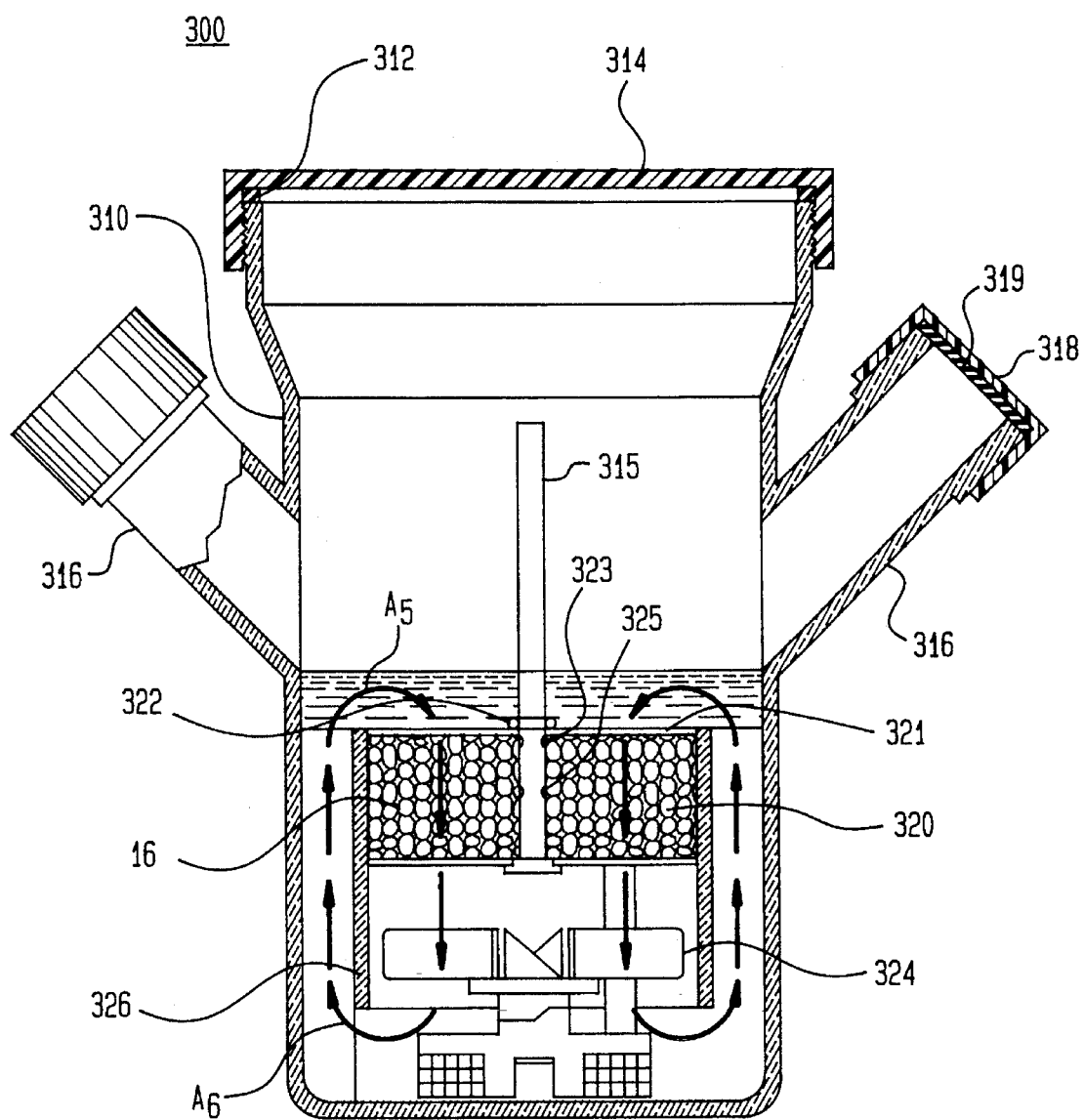
FIG. 3 is a front elevational view of a third embodiment of the reactor of the present invention.

FIG. 3 illustrates an alternate reactor 300 of a third embodiment of the present invention. Vessel 310 houses a packed bed 320 of carrier material 16. Top cap 314 is attached with gasket 312 to vessel 310. A pair of side ports 316 are positioned on either side of vessel 310. Side ports 316 can be used for sampling and changing media. Side cap 318 covers membrane 319. Side cap 318 provides a sterile seal of vessel 310.

O-ring 322 attaches screen cover 321 to base 315. Grooves 323 and 325 are formed in base 315. Screen cover 321 can be attached with O ring 322 either to groove 323 or groove 325 for altering the volume of packed bed 320. Preferably, the basket volume is about 100 ml for holding 10 grams of carrier 16 when screen 321 is attached to groove 323 and the basket volume is about 50 ml for holding 5 grams of carrier 16 when screen 321 is attached to groove 325. Preferably, the working volume of vessel 310 is about 500 mls with a total volume of about 1000 mls.

An impeller 324 is driven by a magnet for providing flow in the direction of arrows $A_5$ and $A_6$ from the top of packed reactor bed 320 towards impeller 324.

Attached metabolites can be easily removed with carrier material 16 without filtering from the system. The reactor of the present invention has the advantage that separation of cells from secreted proteins and waste products is simplified because they remain trapped in carrier material 16 during perfusion. The reactor provides a high surface to volume ratio for cell growth and avoids exposure of cells to gas liquid interfacial forces and shear from the impeller. Anchorage dependent cells attach to the surface of carrier material 16. Cells grown in suspension are retained within the packed bed of carrier material 16.

The reactor of the present invention has the advantage that separation of cells from secreted proteins and waste products is simplified since both anchorage-dependent and suspension cells remain trapped in carrier material 16 during the culture process.

Many anchorage dependent cell lines have been attached to carrier material 16. These include: VERO. Surprisingly, many suspension lines have also been attached to the carrier material 16 such as: hydridomas e.g.: DA 4.4; and insect lines e.g.: TN-368 and Sf–9. Those skilled in the art would recognize that other types of cells can be propagated with the reactors of the present invention.

Figure 5:
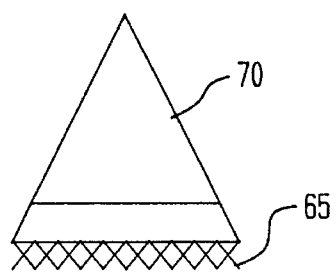
FIG. 5 is a top plan view of a triangular shaped carrier.
Figure 6:
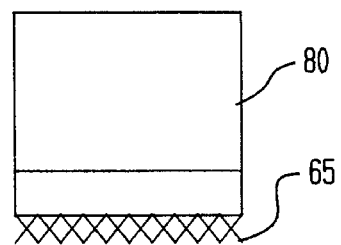
FIG. 6 is a top plan view of a square shaped carrier.
Figure 7:
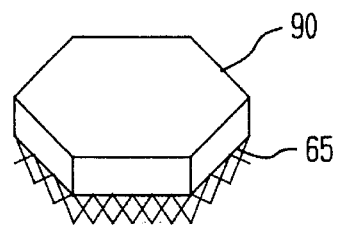
FIG. 7 is a top plan view of a hexagonal shaped carrier.

FIGS. 5–8 illustrate alternate shapes of carrier 16. Upper surface 70 of carrier 16 can have a triangular shape as shown in FIG. 5, or upper surface 80 can have a square shape, as shown in FIG. 6. Alternatively, upper surface 90 of carrier 16 can have a hexagonal shape, as shown in FIG. 7. In the above carriers, lower surface 65 is correspondingly shaped to the shape of the upper surface. It will be appreciated that other shapes could be used for carrier 16.

Figure 8A:
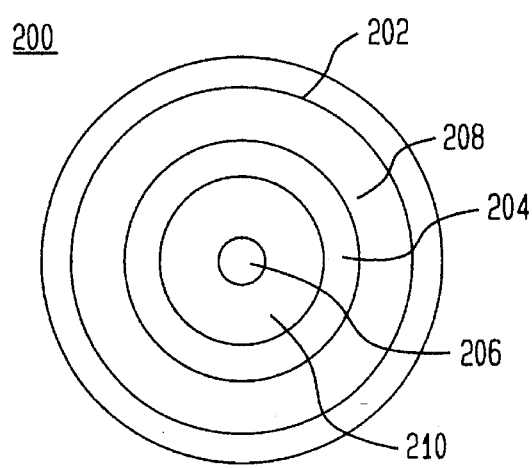
FIG. 8A is a top plan view of a carrier having a plurality of contoured surfaces.
Figure 8B:
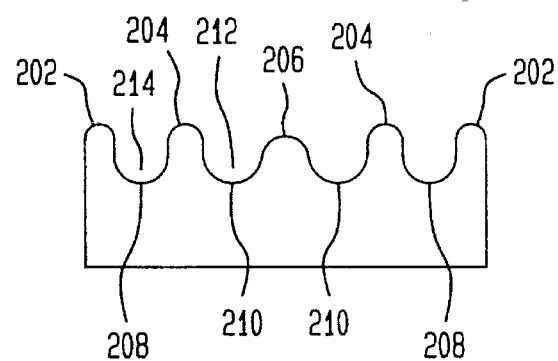
FIG. 8B is a side elevational view of the carrier shown in FIG. 8A.

FIGS. 8A and 8B illustrate an alternative embodiment of the carrier shown as carrier 200. Concentric contoured upper surface 202, 204, 206 are raised above respective lower surfaces 208 and 210. This embodiment has the advantage of channelling of medium in grooves 212 and 214.

The reactor design of the present invention has the advantage of reducing channelling through the packed bed and providing uniformity of flow in the reactor. The use of the carrier in a packed bed has the advantage of supporting propagation of hybridomas and promoting cell growth at a high cell density per unit of the reactor. Hybridomas can be retained within the packed bed of carrier material in a productive state under perfusion with low levels of serum or serum free medium. The reactor is capable of being easily scaled-up because of the low pressure drop across the basket.

EXAMPLE 1

To illustrate the use of the reactor of the present invention for growth of cells or cell cultures, the reactor is packed with polyester non-woven disk carrier. 110 grams of polyester disks were packed into the reactor basket. Cells are mouse-mouse hybridoma, DA4.4 (ATCC HB-57) producing an IgG1 against human IgM. Dulbecco's modified Eagle medium (DMEM) was used for growth of cells in the reactor. Additional supplements were added:

Primatone RL (Sheffield) 2.5 g/L

Oxalacetic Acid 150 mg/L

Mercaptoethanol 3.92 mg/L

Insulin 75.5 µg/L

Sodium Pyruvate 110 mg/L

Streptomycin 100 mg/L

Penicillin 100 Units/L

Bovine Calf Serum (Hyclone) 5% by Volume

PBS (without $Ca^{+2}$, $Mg^{+2}$) was added as media to the vessel and the cover is attached to the vessel. Media was added and incubated overnight. The reactor was seeded.

The culture conditions were as follows:

Temperature 37° C.

Agitation 60–140 rpm

Top Dissolved Oxygen (DO) 50%

Bottom DO >25% pH 7.2

Medium flowrate 45–100 ml/sec

During cultivation, samples were taken and analyzed off-line. Glucose, Lactate and Ammonia concentrations of the medium were determined by enzymatic assays (Sigma Chemical Co.). Monoclonal antibody concentration was determined by radial immunodiffusion assay. Trypan blue cell counts and citric acid/crystal violet nucleus counts by hemocytometer were used to determine the cell numbers in the media and attached to the carrier respectively.

EXAMPLE 2

Cell Attachment

The cell attachment rate in the reactor was determined. After inoculation, cells were maintained in the medium without perfusion to allow the cells to attach to the carrier material 16 inside the basket. The following table illustrates the DA 4.4 cell attachment in the reactor.

TABLE

| Inoculation Cells (cells/ml) | After 5 hours cells attached to material 16 (% of inoculum) | After one day cells attached to material 16 (% of inoculum) | After 30 days cells attached to material 16 (% of inoculum) |
| --- | --- | --- | --- |
| $1.7 \times 10^5$ | 97.1 | 99.5 | 99.9 |

These results indicate that the hybridoma cells were easily trapped in the disk carrier, even if continuous stirring was used during the attachment period.

EXAMPLE 3

Cell cultivation was operated for 36 days for hybridoma 123A producing an IgG type antibody against human gamma interferon. Nuclear counting was performed after the reactor was disassembled. The calculated values indicated an inoculum concentration of $1.8 \times 10^6$ cells/$cm^3$ in the packed bed of material 16 and $9.4 \times 10^7$ cells/$cm^3$ at the end of the experiment. In addition, $5 \times 10^4$ cells/ml were measured in the supernatant which represents less than 0.1% of the cells in the reactor.

EXAMPLE 4

Comparison of Cell Growth and Productivity

Figure 9:
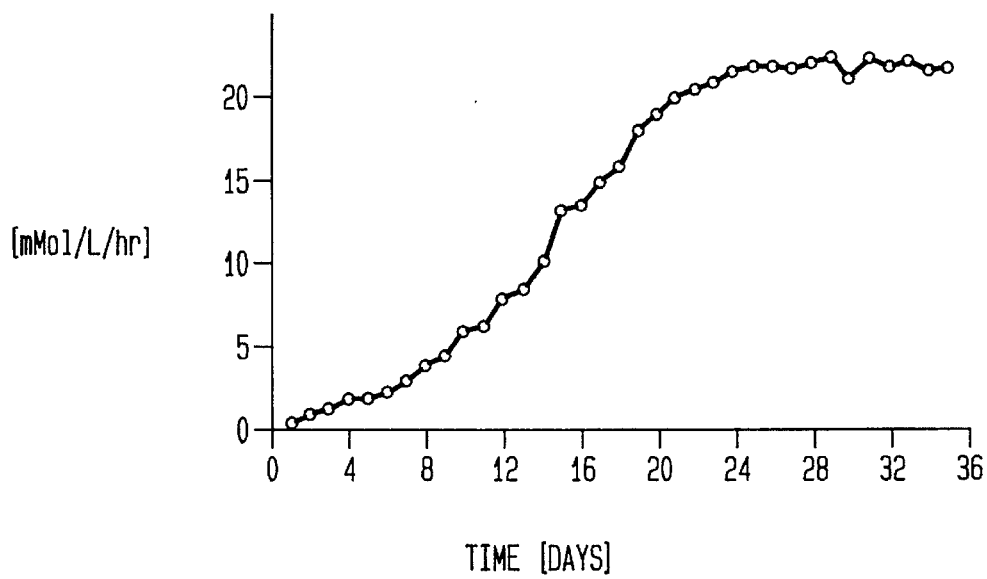
FIG. 9 is a graph of results for oxygen uptake in the reactor of the present invention.

FIG. 9 illustrates oxygen uptake rate during hybridoma 123A cell cultivation with a packed bed reactor of the present invention. The dissolved oxygen concentrated at the top of the basket was controlled at 50% by gas flow rate and the dissolved oxygen content at the bottom of the basket was greater than 25% by liquid flow via the impeller.

The following table illustrates MAb productivity for various modes of production for the culture of 123A cells.

| MODE OF CELL CULTIVATION | | PRODUCT YIELD (mg/day/L) |
| --- | --- | --- |
| Repeated batch | T-Flask | 23 |
| Suspension | Stirred Tank | 20 |
| Perfusion | Packed-bed | 277 |
| Immobilization | Reactor | |

The results indicate a 14 fold increase for the packed bed reactor of the present invention as compared to a stirred-tank reactor.

Figure 10:
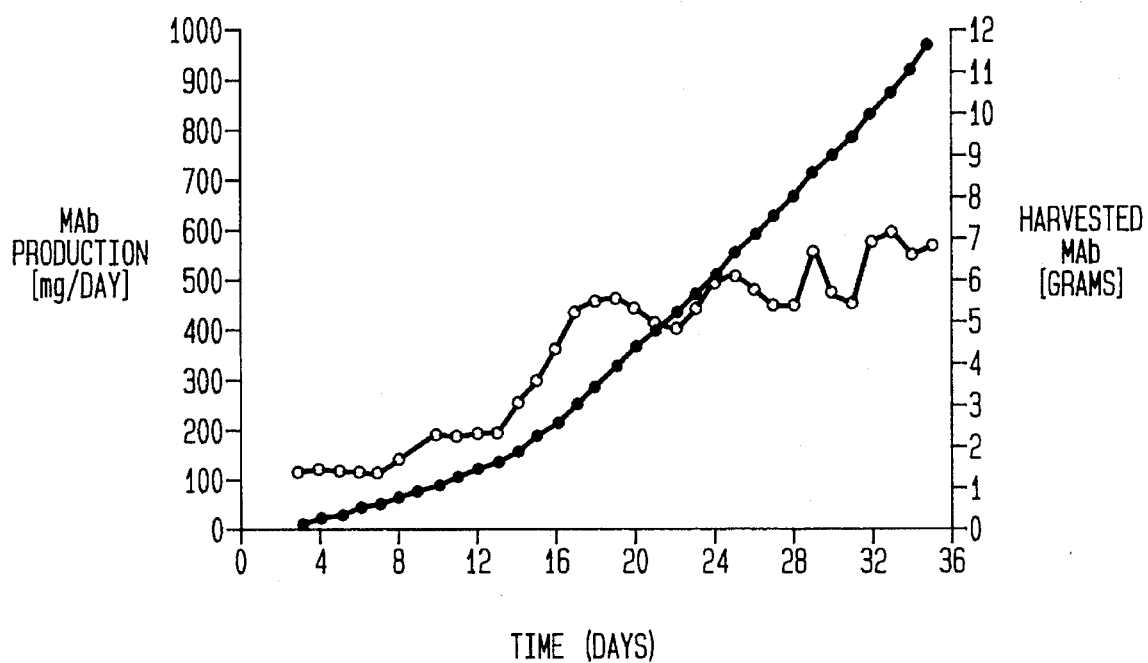
FIG. 10 is a graph of results for Mab production and harvested Mab.

FIG. 10 illustrates MAb production from hybridoma 123A in a packed bed reactor system. MAb produced was about 0.5 grams per day during the production phase and total yield was about 11.5 grams.

EXAMPLE 5

Anchorage—Dependent Cell Culture rCHO cell line was cultivated in the reactor for 24 days. DMEM/F12 culture medium was used with supplements of 1–5% calf serum. The total volume of the reactor was 2.2 liters, packed by 65 grams carrier material 16. Culture condition was: temperature 37° C., pH 7.2, dissolved oxygen concentration 50%, perfusion rate was maintained at 3.0–3.4 liter per day since day 7. The continuous operation led to a 60 fold increase in cell density reaching $1.2 \times 10^8$ cells per $cm^3$ of bed volume at the end of a 24 day run.

EXAMPLE 6

The average shear stress ($\tau$ avg) on the surface of the cells in the packed-bed can also be estimated by the following equation.

$$\tau \text{ avg} = \frac{\Delta p}{L_b(S/V)}$$

where $\Delta p$ is the pressure drop in the bed; $L_b$ the height of the bed; and S/V the fiber surface-to-volume ratio of the bed reactor. The calculated $\tau$ avg. at liquid velocity of $_{1.0}$ cm/s was found to be 0.6 dyn/$cm^2$. The shear stress is significantly lower than what is needed to cause shear damage to the cells.

A pitot tubing method was used to determine liquid flow rate for the reactor shown in FIG. 2. A tracer (acid and base) method was also used to measure liquid flow rate.

Figure 11:
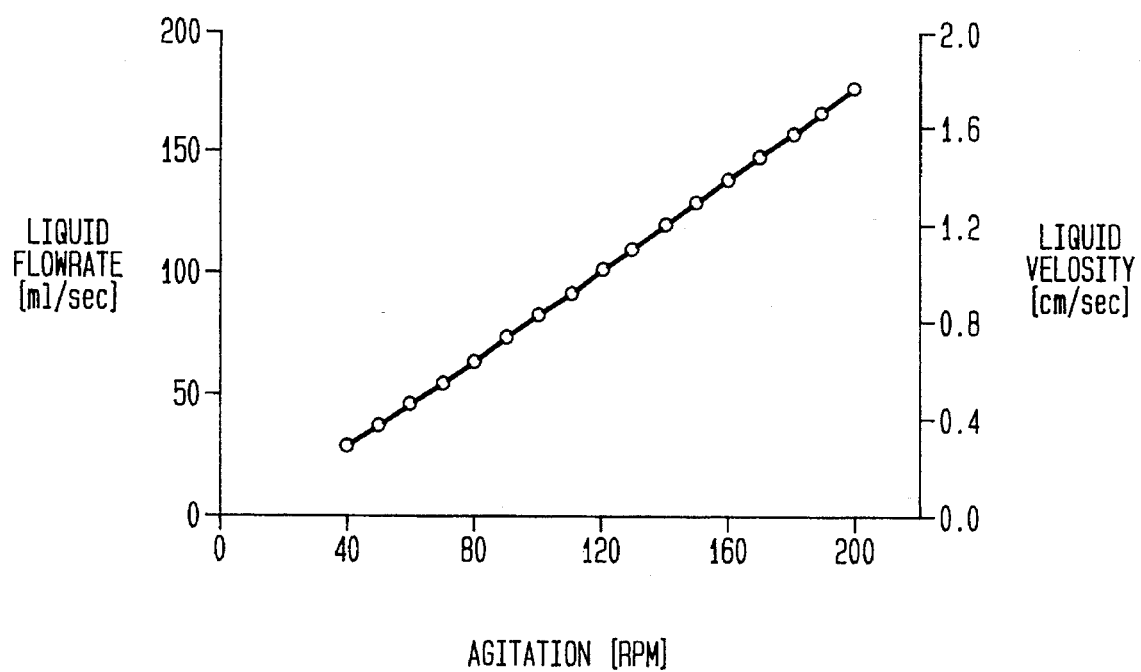
FIG. 11 is a graph of impeller speed versus flow rate for the reactor of the present invention.

A 2.2 liter reactor as shown in FIG. 2 was used. The cross section surface of the packed bed was 100 $cm^2$. The superficial velocity was measured to be 0.65 cm/s to 1.76 cm/s at impeller speeds of 80–200 rpm as shown in FIG. 11. These results indicate that the liquid flow rate provided by the impeller is sufficient and meets the oxygen and nutrient demands of the immobilized cells.

Pressure drop of the disk bed, $\Delta p$, was measured with a glass tube manometer at different liquid flow rates and was calculated by the equation:

$$\Delta p = \Delta h(\sigma_L - \sigma_o)g = k\mu Lu$$

where $\Delta h$ is manometer reading (cm); $\sigma_L$ is density of liquid (g/$cm^3$); $\sigma_o$ is density of air (g/$cm^3$); g is gravity acceleration (cm/$s^2$); $\mu$ superficial viscosity (poise). The resistance coefficient of the disk bed, k, was calculated from pressure drop measurements to be $2 \times 10^4$ $cm^2$.

Low pressure drops provide for scale-up of the reactor. A volume of 1 to 1000 L can be used in the reactor while maintaining cell densities.

EXAMPLE 7

It is known that insect cells are shear sensitive and can be damaged by gas sparging. It is also known that insect cells have a high oxygen demand in comparison to mammalian cells.

To illustrate the use of the reactor of the present invention for growth of insect cell lines, the reactor shown in FIG. 2 was used for a TN-368 cell line. A serum free medium Ex-cell 400 manufactured by JRH Bioscience, Kansas was used with the reactor. The growth media was added to the reactor and the reactor contents were incubated overnight. The following is a table of the volume of the reactor.

Equipment: 2.2 liter basket reactor
    Working volume: 1.3 liter
    Total volume: 2.2 liter
    Basket volume: 0.65 liter
    Carrier: Material 16
    Weight: 65 grams Inoculation conditions were pH 6.2, temperature 27° C., dissolved oxygen 50%. After one hour of inoculation all cells were attached to the carrier in the packed bed in the basket. Glucose concentration decreased from 2.0 g/liter to 0.83 g/liter during the first two days. Perfusion was initiated on day 3 at 1.05 liters per day. From day 9 to day 13 the perfusion rate was maintained at 1.53 liters per day.

Trypan blue cell counting was performed after 13 days. The total cells in the 0.65 liter packed bed was $5.6 \times 10^{10}$ and the cell density was $8.6 \times 10^7$. This results in a cell density that is 20 times greater as compared to conventional suspension batch culture systems. The cells were distributed uniformly in the carrier of the packed bed.

The present invention has the advantage of promoting cell growth on a carrier while producing gentle flow of growth medium over the carrier. Both anchorage and suspension cells are entrapped within a carrier. The carrier provides a high surface to volume ratio for cell growth which results in high cell densities and a carrier having a contoured surface promotes attachment and continuous growth of hybridoma cells, thereby having high Mab production rates. The reactor provides gentle flow of medium downwardly through a basket containing the carrier for reducing removal of cells from the carrier. Scale up is possible due to the low pressure drop across the basket and column, and oxygen uptake rate can be calculated and used to optimize perfusion. The reactor can be used with a variety of anchorage dependent cells and suspension cells.

While the invention has been described with reference to the preferred embodiment thereof, it will be appreciated by those of ordinary skill in the art that modifications can be made to the structure and form of the invention without departing from the spirit and scope thereof.

We claim:

1. An apparatus for use in the cultivation of cells comprising:

a vessel having an upper portion, a closed bottom portion and side walls extending from said closed bottom portion;

a hollow tube positioned in said vessel having a lower open end;

a basket including a top and a bottom portion with holes therethrough, said basket extending around said hollow tube to the side walls of said vessel;

means for introducing gas bubbles in said vessel; and agitator means for fluid flow affixed to said hollow tube, said agitator means including tubulation means having an input opening coupled to said hollow tube and an exit opening, said fluid being circulated by said agitator means for providing substantially bubble-free fluid to said basket, wherein said gas bubbles rise towards said upper portion of said vessel and said substantially bubble free fluid flows from said bottom portion of said vessel through said hollow tube to the top of said vessel and returns to said bottom portion of said vessel through said basket.

2. The apparatus of claim 1 wherein said basket includes an upper and lower screen forming said top and bottom portion of said basket.

3. The apparatus of claim 2 further comprising a removable cover attached to a top portion of said vessel and a reaction medium inlet positioned through said cover.

4. The apparatus of claim 3 wherein said means for introducing gas bubbles comprises a sparger positioned at the lower open end of said hollow tube.

5. The apparatus of claim 4 further comprising a carrier positioned in said basket, said carrier having a first surface formed of a non-woven screen material and a second surface formed of a non-woven material, said second surface being contoured and raised above said first surface wherein cells are immobilized on said carrier.

6. A method for the cultivation of cells comprising the steps of:

placing a carrier within a basket, said basket positioned within a vessel;

adding cells to said basket, said cells being immobilized on said carrier;

introducing gas bubbles directly in said vessel to said basket, said vessel having a bottom and top portion; and circulating substantially bubble-free medium through the basket, said gas bubbles rise towards said top portion of said vessel and said bubble-free medium flows to the bottom of said vessel through said basket for providing bubble-free flow said circulating step being carried out with an agitator means, said basket including a hollow tube, said agitator means including tubulation means, said tubulation means having an inlet attached to said hollow tube and an outlet, wherein fluid flows from the bottom of said vessel through said hollow tube to said inlet and through said outlet of said tubulation means to the top of said vessel and returns to the bottom of said vessel through said basket.

7. An apparatus for use in cells cultivating comprising:

a vessel having a closed bottom portion and side walls extending from said closed bottom portion;

basket means having a top and a bottom portion with holes therethrough and side portions positioned between said top and bottom portions, said basket means positioned in said vessel;

means for introducing gas bubbles into said vessel comprising a sprager; and means for circulating fluid through said basket means, said means for circulating fluid providing substantially bubble-free fluid to said basket means, said substantially bubble-free fluid flows from said top of said vessel to said bottom of said vessel through said basket means wherein said basket means includes:

an upper and lower screen forming said top and said bottom portion of said basket means; and a base including a plurality of grooves, said upper screen being received in said one of said grooves, wherein alternating the placement of said upper screen in said grooves alters the volume within said basket means.

8. The apparatus of claim 7 wherein said means for circulating fluid comprises:

an impeller; and, magnetic means for driving said impeller.

9. The apparatus of claim 8 further comprising:

a carrier positioned in said basket means, said carrier having a first surface formed of a non-woven screen material and a second surface formed of a non-woven material, said second surface of said carrier being contoured and raised above said first surface, wherein said cells are immobilized on said carrier.

10. An apparatus for use in the cultivation of cells comprising:

a vessel having an upper portion, a closed bottom portion and sidewalls extending from said closed bottom portion;

a hollow tube positioned in said vessel having a lower open end;

a basket including a top and a bottom portion with holes therethrough, said basket extending around said hollow tube to the sidewalls of said vessel; and, agitator means for fluid flow affixed to said hollow tube, said agitator means including tubulation means for fluid flow having an input opening coupled to said hollow tube and an exit opening, wherein fluid flows from said bottom of said vessel through said hollow tube to the top of said vessel and returns to the bottom portion of said vessel through said basket.

11. An apparatus for use in the cultivation of cells comprising:

a vessel having an upper portion, a closed bottom portion and sidewalls extending from said closed bottom portion;

a hollow tube positioned in said vessel having a lower open end;

a basket including a top and a bottom portion with holes therethrough, said basket extending around said hollow tube toward the sidewalls of said vessel;

means for introducing gas bubbles in said vessel;

agitator means for driving fluid flow up said hollow tube; and, flow directing means attached to said hollow tube and having an input opening coupled to said hollow tube and an exit opening, said fluid being circulated by said agitator means for providing substantially bubble-free fluid to said basket, wherein gas bubbles rise toward said upper portion of said vessel and said substantially bubble-free fluid flows from said bottom portion of said vessel through said hollow tube to the top of said vessel and returns to the bottom portion of said vessel through said basket.

12. A method for the cultivation of cells comprising the steps of:

placing a carrier within a basket, said basket positioned within a vessel;

adding cells to said basket, said cells being immobilized on said carrier;

introducing gas bubbles directly in said vessel to said basket, said vessel having a bottom and top portion; and, circulating substantially bubble-free medium through the basket, said gas bubbles rising toward said top of said vessel and bubble-free medium flowing to the bottom of said vessel through said basket for providing bubble-free flow, said circulating step being carried out with an agitator means for driving said medium through a hollow tube surrounded by said basket, flow directing means connected to said hollow tube, said flow directing means having an inlet attached to said hollow tube and an outlet, wherein fluid flows from the bottom of said vessel through said hollow tube to said inlet and through said outlet of said flow directing means to the top of said vessel and returns to the bottom of said vessel through said basket.

* * * * *